US008460382B2

(12) United States Patent
Helm et al.

(10) Patent No.: US 8,460,382 B2
(45) Date of Patent: Jun. 11, 2013

(54) METHOD AND SYSTEM FOR FUSING A SPINAL REGION

(75) Inventors: Gregory A. Helm, Ruckersville, VA (US); David F. Kallmes, Rochester, MN (US); Gerald R. Hankins, Charlottesville, VA (US); Mary E. Jensen, Afton, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 112 days.

(21) Appl. No.: 13/087,194

(22) Filed: Apr. 14, 2011

(65) Prior Publication Data
US 2011/0196497 A1 Aug. 11, 2011

Related U.S. Application Data

(62) Division of application No. 10/936,758, filed on Sep. 8, 2004, now Pat. No. 7,947,079, which is a division of application No. 09/959,798, filed as application No. PCT/US00/12407 on May 8, 2000, now Pat. No. 6,805,697.

(60) Provisional application No. 60/133,032, filed on May 7, 1999, provisional application No. 60/133,033, filed on May 7, 1999.

(51) Int. Cl.
*A61F 2/44* (2006.01)
(52) U.S. Cl.
USPC ........................................ 623/17.12; 606/170

(58) Field of Classification Search
USPC ................ 623/17.11, 17.12; 606/79–81, 170, 606/171, 178, 179–183
See application file for complete search history.

(56) References Cited

U.S. PATENT DOCUMENTS

| 3,875,959 | A |   | 4/1975  | Bouteille |
|-----------|---|---|---------|-----------|
| 4,751,922 | A |   | 6/1988  | DiPietropolo .................. 606/80 |
| 4,969,888 | A |   | 11/1990 | Scholten et al. ................ 606/94 |
| 5,013,317 | A |   | 5/1991  | Cole et al. |
| 5,015,255 | A |   | 5/1991  | Kuslich ......................... 128/898 |
| 5,192,282 | A |   | 3/1993  | Draenert |
| 5,411,503 | A |   | 5/1995  | Hollstien et al. |
| 5,489,307 | A |   | 2/1996  | Kuslich et al. ................ 128/898 |
| 5,499,984 | A |   | 3/1996  | Steiner et al. ................... 606/80 |
| 5,527,316 | A |   | 6/1996  | Stone et al. |
| 5,549,679 | A | * | 8/1996  | Kuslich ..................... 623/17.12 |
| 5,624,447 | A |   | 4/1997  | Myers |
| 5,662,580 | A |   | 9/1997  | Bradshaw et al. ................ 600/3 |

(Continued)

*Primary Examiner* — Eduardo C Robert
*Assistant Examiner* — Tara Carter
(74) *Attorney, Agent, or Firm* — Novak Druce Connolly Bove + Quigg LLP; Vincent M DeLuca; Robert J. Decker

(57) ABSTRACT

A method and system for fusing a region in the spine involve the use of at least one guide tube to pass instruments and substances into the spinal region in a minimally invasive manner. In the preferred practice of the method, a guide tube is anchored to a vertebra and the guide tube is moved to thereby position the vertebra. A steerable drilling tool is passed through the guide tube and steered into position to abrade at least a portion of an intervertebral disc and thereby create a cavity in the disc. A flowable substance is passed into the cavity and permitted to solidify to establish fusion in the cavity. Optionally, an uninflated balloon is inserted into the cavity and the balloon is filled with the flowable substance to contain the flowable substance.

6 Claims, 17 Drawing Sheets

U.S. PATENT DOCUMENTS

| | | | |
|---|---|---|---|
| 5,720,749 A | 2/1998 | Rupp | 606/79 |
| 5,888,220 A | 3/1999 | Felt et al. | 128/898 |
| 6,063,088 A | 5/2000 | Winslow | 606/61 |
| 6,086,589 A | 7/2000 | Kuslich et al. | 606/247 |
| 6,440,138 B1 * | 8/2002 | Reiley et al. | 606/79 |
| 6,490,467 B1 | 12/2002 | Bucholz et al. | 600/407 |
| 6,491,699 B1 | 12/2002 | Henderson et al. | 606/130 |

* cited by examiner

METHOD AND SYSTEM FOR FUSING A SPINAL REGION

This application relies on the benefit of priority of U.S. provisional patent application Ser. No. 60/133,032 and U.S. provisional patent application Ser. No. 60/133,033, both filed on May 7, 1999. These two applications are incorporated herein by reference.

BACKGROUND OF THE INVENTION

1. Field of the Invention

The present invention relates to a method and system for fusing a spinal region. More particularly, the present invention relates to minimally invasive intravertebral disc distraction, rotation, or translation, removal of disc and/or vertebral bone material, and subsequent fusion of a disc.

2. Description of Related Art

There are five movable vertebrae in the lower back. This area is called the lumbar spine and is the flexible part of the back. Above the lumbar spine is the thoracic spine and below it is the sacrum and coccyx. Between each vertebra is a cushion referred to as an intervertebral disc. Each disc has a tough exterior rim of fibrous cartilage (similar to that of a radial tire), referred to as the annulus fibrosis. Within each disc is a resilient and "jelly-like" interior filling, referred to as the nucleus pulposus. The top and bottom of the disc are covered by relatively bony endplates.

FIG. 1 is a partial cross-section view of a portion of the spine. As shown in this figure, an intervertebral disc D is positioned between adjacent vetebral bodies V1 and V2 and includes an annulus fibrosis A, a nucleus pulposus N, and end plates EP. Positioned on the vertebral bodies V1 and V2 are a superior articular process SAP, a pedicle P, an inferior articular process IAP, a spinal process SP, and a facet joint FJ.

Each disc and the vertebra above and below it compromise a motion segment. Movement such as bending forward (flexion) bending backwards (extension) and twisting and turning (rotation) occur at these motion segments.

Approximately 80% of the American population experiences various forms of lower back pain at some point during their lifetimes. Back pain is sometimes associated with intervertebral disc trauma, degeneration of the disc or joints in the spine, disc herniation, spinal instability, bone spurs, or inflamed ligaments. Back pain can also be caused by an injury, disease, malalignment, tumor, hereditary weakness, and previous back surgery. In addition, back and/or leg pain may be caused by pressure on the spinal cord or on a spinal nerve. Techniques for treatment vary from simple interventions such as rest and physical therapy to more complicated surgical procedures such as spinal fusions. (As used herein the term "fusion" refers in general to increasing the stability of a region of the spine, and does not necessarily require the physical joining of portions of the spine.) Some surgical techniques have improved to the point where invasiveness and trauma to non-spinal tissues can be kept to a minimum.

Intervertebral discs commonly wear and tear, weakening their outer fibrous structure. Increasing pressure in the spine may bulge and even rupture the disc, causing back or leg pain. In normal aging, discs lose water and decrease their ability to function as "shock absorbers." Narrowing discs increase stress to the facet joints.

Instability or abnormal motion may occur in the advanced stages of arthritis or from trauma. Spondylolithesis is a forward slipping of one vertebra over another and may result of severe instability. Spinal stenosis, a narrowing of the spinal canal, may be a result of arthritis, putting pressure on the nerves or the spinal cord. Osteoarthritis may result in narrowing of the disc spaces and development of bone spurs on the vertebral bodies.

Herniated discs are another form of injury to the intravertebral disc and are often referred to as "slipped discs." This term is derived from the action of the nucleus tissue when it is forced from the center of the disc. The disc itself does not slip. However, the nucleus tissues located in the center of the disc can be placed under so much pressure that it can cause the annulus to be herniated or rupture against one or more of the spinal nerves which can cause pain, numbness, or weakness in the lower back, leg or foot. Other names used for herniated discs are "prolapsed," "bulging," or "ruptured." Depending on the results of a physical examination and the severity of the condition, physicians commonly offer one of two forms of treatment. The first common treatment is "conservative therapy," comprising bed rest, pain medication, and physiotherapy.

If conservative therapy does not bring enough pain relief, surgical procedures are typically considered. The most common reason for recommending lower back surgery is to relieve either back or leg pain. To decrease leg pain, pressure is removed from the affected spinal nerve. Removal of a tumor, treatment of a fractured spine, and repair of malalignments are other reasons surgery is undertaken. In order to accomplish these objectives, the spine surgeon may remove the disc (discectomy) or a part of the lamina (laminotomy) or remove the whole lamina (laminectomy). The procedure is also referred to as a decompression because the pressure on the nerve or the spinal cord or cauda equina is removed.

Sometimes motion between the vertebral bodies must also be stopped in an effort to relieve pain. In such cases, the surgeon may elect to perform a spinal fusion procedure. This procedure entails implanting pieces of bone graft, usually obtained from the patient's own iliac crest bone (hip). The bone graft is intended to encourage bone growth between the vertebral bodies and the posterior aspect of the spine. If the bone develops and grows between the vertebrae, then the spine segment is said to have "fused," and the motion between the vertebral bodies is therefore eliminated.

Fusion is best accomplished when the vertebrae are kept as motionless as possible during the healing process which is usually four to six months. Physicians may recommend achieving stability through additional internal fixation devices attached to the vertebral bodies during the surgical procedure. This may be performed with a combination of screws inserted meticulously into the vertebral body and attached to one another with a series of rods, plates, wires, or hooks.

Until a few years ago, the only surgical treatment for herniated lumbar discs was the open removal of a part of the herniated disc, an often effective but major operation that requires general anesthesia, the dissection of muscle, removal of bone, and at times, bone fusion. These procedures increase the risk to the patient of post-operative complications.

In recent years, techniques employing the use of endoscopy have been incorporated into lumbar spine surgery making minimally invasive spine surgery possible while overcoming disadvantages of traditional techniques. Endoscopic discectomy can provide an effective way to decompress and repair damaged discs without open surgery. An endoscope provides clear visualization and magnification of deep structures. First used in knee surgery, endoscopy (arthroscopy), with its advanced miniaturization and video imaging technology, has made it possible for a less invasive and less traumatic discectomy procedure for some disc patients.

Endoscopic discectomy is an outpatient surgical procedure to remove herniated disc material. Using local anesthesia with the help of x-ray flouroscopy and magnified video for guidance, a small specially-designed endoscopic probe is inserted through the skin of the back, between the vertebrae, and into the herniated disc space. Tiny surgical attachments are then sent down the hollow center of the probe to remove a portion of the offending disc. The microsurgical attachments can also sometimes be used to push the bulging disc back into place and for the removal of disc fragments and small bony spurs.

Endoscopic discectomy is different from open lumbar disc surgery because there is no traumatic back muscle dissection, bone removal, or large skin incision. The risk of complications from scarring, blood loss, infection, and anesthesia that may occur with conventional surgery are drastically reduced or eliminated with this procedure. Endoscopic discectomy was invented to be an effective treatment for herniated discs while avoiding these risks.

A wide variety of spinal implants are available to the clinician for the surgical treatment of spinal disorders. Most of the implants are designed to promote long term fusion. For certain conditions, anterior fusion of the lumbar spine is a standard operation. Despite improvements in fusion techniques and reductions in the pseudoarthritis rate, improved procedures and devices are needed. Surgeons specializing in operations on the vertebral column necessarily incorporate laparoscopic surgery. Other concepts such as the biological enhancement of spinal fusion and alternatives to fusion such as artificial discs and interbody cage devices are the object of intense, multidisciplinary study. Despite these improvements, currently there are neither devices designed to distract the intervertebral disc percutaneously nor minimally invasive procedures to achieve spinal fusions.

In light of the foregoing, there is a need in the art for improving procedures and devices associated with performing spinal surgery.

SUMMARY OF THE INVENTION

Accordingly, the present invention is directed to a method and apparatus that substantially obviate one or more of the limitations of the related art. To achieve these and other advantages and in accordance with the purposes of the invention, as embodied and broadly described herein, the invention includes a method of fusing a spinal region. In the method, a guide tube is contacted against at least one vertebra, and a steerable drilling tool is inserted through the guide tube. The steerable drilling tool is steered toward a disc and at least a portion of the end plates of the disc are abraded with the drilling tool. At least the abraded end plates of the disc and a nucleus of the disc are removed to form a cavity extending in at least the disc. A flowable fusion substance is passed into the cavity. The fusion substance solidifies to provide fusion in the cavity.

In one aspect of the invention, the method includes inserting an inflatable implant in the cavity, and the flowing of the flowable fusion substance includes passing the fusion substance into the inflatable implant to inflate the implant in the cavity.

In another aspect, the method includes inserting a balloon into the cavity, inflating the balloon with a contrast agent, and viewing the balloon with imaging equipment to evaluate the cavity. The balloon is then optionally removed or used to contain the flowable infusion substance.

In a further aspect, the guide tube and/or the drilling tool has a tracking element, and a location of the guide tube and/or drilling element is determined relative to a known reference point with a computer-controlled surgical navigation system.

In the preferred practice of the invention, at least an annular portion of the annulus fibrosis of the disc remains intact throughout the procedure. In addition, the method preferably involves abrading material in the medullary area of the vertebra.

Another aspect of the invention involves a method wherein a guide tube is releasably anchored in at least one vertebra. There are various releasable anchoring structures that could be provided on the guide tube. In the preferred embodiment, an insertion end of the guide tube includes at least one thread permitting threading of the guide tube in the at least one vertebra.

In still another aspect, the guide tube is moved when the guide tube is anchored in the vertebra to thereby position the vertebra. The movement of the guide tube could include distracting the vertebra away from the disc and/or rotating the vertebra. Preferably, the location of the guide tube is determined with a computer controlled surgical navigation system.

In yet another aspect, the method includes releasably anchoring a first guide tube in a first vertebra, releasably anchoring a second guide tube in a second vertebra, and moving at least one of the first and second guide tubes to thereby position the first and second vertebrae with respect to one another.

An even further aspect involves a method wherein a balloon is inserted into a cavity extending in at least a disc. The balloon is inflated with a contrast agent and viewed with imaging equipment to evaluate the cavity. The contrast agent is then preferably removed from the balloon, and a flowable fusion substance is flowed into the cavity. Optionally, the balloon could be an inflatable implant which is inflated with the fusion substance. Alternatively, the balloon could be removed from the cavity and an inflatable implant could be placed in the cavity and filled with the fusion substance.

According to another aspect of the invention, at least a portion of a disc is abraded with a steerable drilling tool, and disc material is removed to form a cavity. An implant is placed in the cavity to provide fusion in the cavity. Preferably, the implant is an inflatable balloon.

One more aspect of the invention involves a system for use in a spinal fusion procedure. The system includes a steerable drilling tool having a rotatable bit configured to abrade at least one of vertebral material and disc material, and at least one guide tube having a proximal end portion, a distal end portion, and at least one lumen extending from the proximal end to the distal end, the lumen being configured to allow for passage of the steerable drilling tool therethrough. In addition, the system could include one or more inflatable balloon implants.

A further aspect of the invention involves the steerable drilling tool alone. In one embodiment, the steerable drilling tool includes a tubular member having at least one axially movable steering element. Axial movement of the steering element varies position of a distal insertion end of the tubular member with respect to a remainder of the tubular member. The drilling tool could further include a flexible, rotatable drive member in the tubular member and a drill bit at a distal insertion end of the drive member. Rotation of the drive member rotates the drill bit. Optionally, the drilling tool also includes a tracking element configured to interact with a computer-controlled surgical navigation system to determine the location of a drill bit relative to a known reference point.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
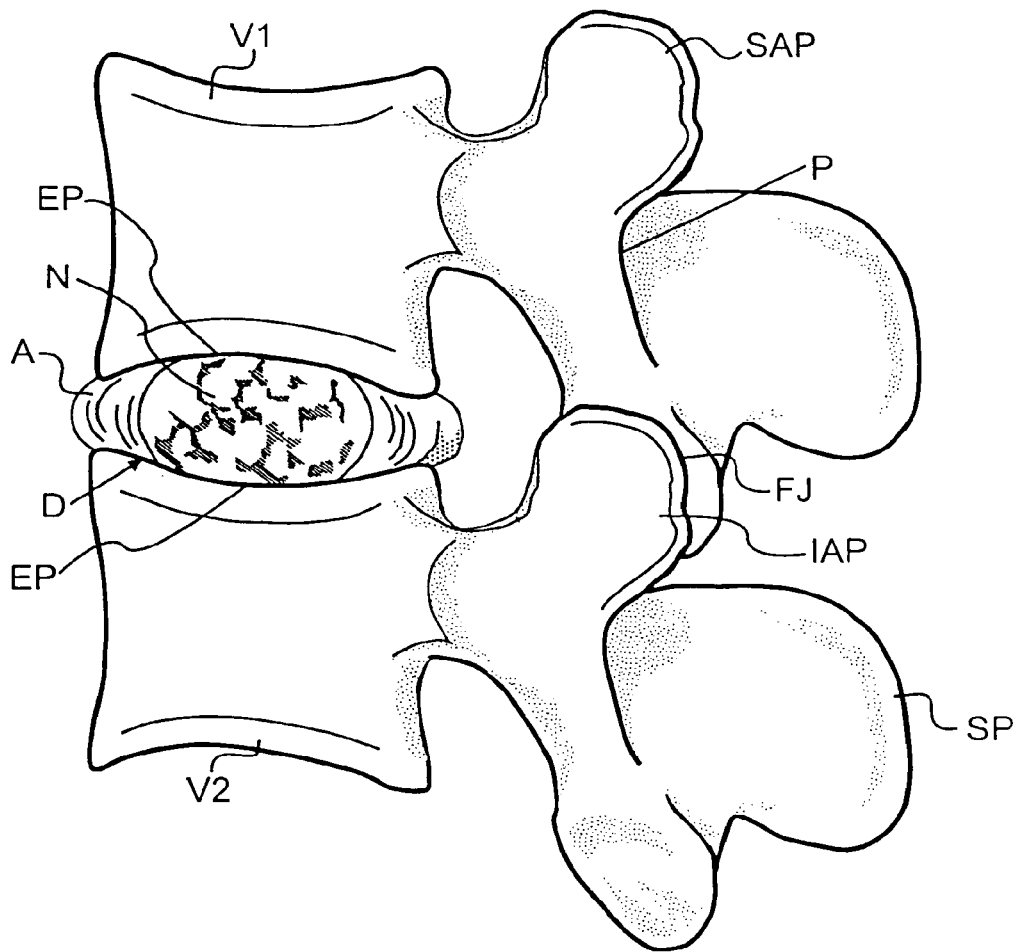
FIG. 1 is a partial cross-section, lateral view of a portion of the spine.

Reference will now be made in detail to the present preferred embodiments of the invention, examples of which are illustrated in the accompanying drawings. Wherever possible, the same reference numbers (optionally including different suffixes) are used in the drawings and the description to refer to the same or like parts.

Figure 2:
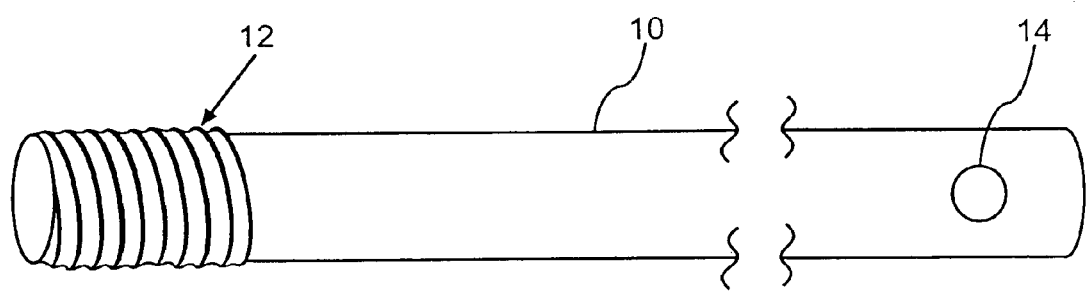
FIG. 2 is a side view of a guide tube in accordance with an embodiment of a system of the present invention.

FIGS. 2, 3, 5, and 10 show examples of components that could be included in an embodiment of a system according to the present invention. As shown in FIG. 2, the system preferably includes at least one guide tube 10 having at least one inner lumen extending from a proximal end portion to a distal end portion. The distal end portion of the guide tube 10 preferably includes a releasable anchoring element 12 for releasably anchoring the distal end portion of the guide tube 10 in at least one vertebra. In the embodiment shown in FIG. 2, the anchoring element 12 is at least one thread on an outer surface of the guide tube 10. The thread permits the guide tube 10 to be removably threaded into a hole bored in a vertebra.

The guide tube 10 is preferably made of stainless, surgical steel but may be made of metal composites, ceramic composites, surgical polymers or surgical plastics.

Preferably, the guide tube 10 includes a suitable tracking element 14 configured to interact with a computer controlled surgical navigation system (not shown) using a detector for determining the position of the guide tube 10 with respect to a known reference in 3D space. By way of example only, the tracking element 14 could be at least one LED emitter/reflector located on a proximal end portion of the guide tube 10. The tracking element 14 could also be any structure that is capable of being detected/tracked by means of a surgical navigation system that uses any sonic, optical, electromagnetic, or other suitable technology known in the art. For example, the tracking element 14 is particularly capable of being used with a surgical navigation system constructed according to the teachings of U.S. Pat. No. 5,383,454; PCT Application No. PCT/U.S.94/04530 (Publication No. WO 94/24933); and/or PCT Application No. PCT/U.S.95/12894 (Publication No. WO 96/11624), the disclosures of which are incorporated by reference.

The guide tube 10 includes a lumen that extends from its proximal end portion to its distal end portion. Preferably, the lumen is sized to allow for passage therethrough of at least one tool, such as the drilling tool 20 shown in FIG. 3. The drilling tool 20 preferably includes a bit 22 (i.e., burr) configured to abrade soft tissue or bone, such as portions of an intervertebral disc or a vertebra. The bit 22 is preferably a high speed drill bit made of hardened surgical, stainless steel and optionally coated with Teflon or other coatings to prevent aggregation or sticking of osseous material. The bit 22 is coupled to a flexible, rotatable drive member 24, such as a cable, that is rotatably driven by an external motor (not shown) to rotate the bit 22. The drive member 24 passes through a tubular member 26 that is preferably configured to be steerable.

Figure 3:
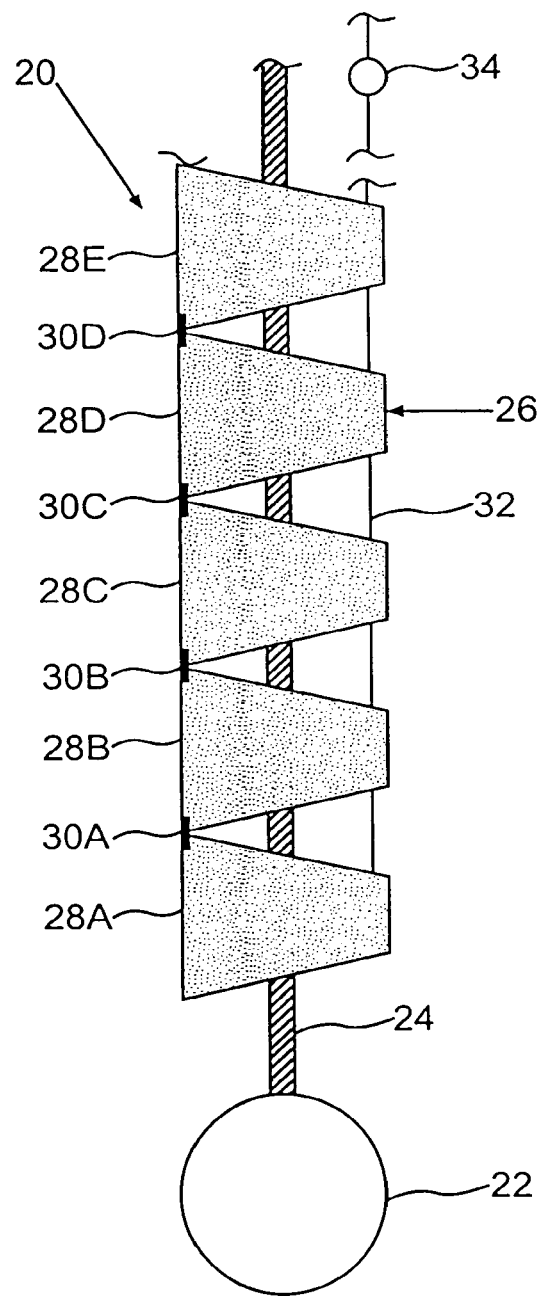
FIG. 3 is a side view of a steerable drilling tool of the system embodiment.

As shown in FIG. 3, the tubular member 26 includes a number of segments 28a-28e. Hinge members 30a, 30b, 30c and 30d couple adjacent pairs of the segments 28a-28b, 28b-28c, 28c-28d, 28d-28e together to permit relative pivotal movement of the segments in each of the pairs. An axially movable steering element 32, such as a cable, passes freely through the segments 28b-28e and has a distal end connected to the distal segment 28a. Axial movement of the steering element 32 causes bending at one or more of the hinge members 30a-30d in a plane to vary the position of the distal end portion of the tubular member 26 with respect to the remainder of the tubular member 26. This enables steerable movement of the drilling tool 20, especially when the movement at the distal end portion is combined with rotation of the tubular member 26 and/or axial movement of the tubular member 26. Of course, there are many different ways in which the drilling tool 20 could be constructed to provide steering.

A tracking element 34 could be provided on the drilling tool 20 to interact with a computer controlled surgical navigation system to determine the location of the bit 22 with respect to a known reference point. For example, the tracking element 34 could be provided on the steering element 32 and constructed like the tracking element 14 shown in FIG. 2.

The drilling tool 20 is preferably made of surgical steel, but the drive member 24 and steering element 32 could be made of metal composites, surgical polymers, or other suitable materials. Preferably, at least a portion of the drilling tool 20 is capable of being imaged with fluoroscopic imaging. The drilling tool 20 could be constructed to be connected to a stereotactic device that could be used to determine the position of the bit 22.

Structure could be provided on the drilling tool 20 to remove materials with suction. For example, the drilling tool could include a lumen capable of being coupled to a suction source. For example, a flexible tube, such as surgical polymer tubing, could be provided in the tubular member and have an open end extending adjacent to the bit 22.

Although the steerable drilling tool 20 is described below as being used in a spinal fusion procedure, the drilling tool 20 could be used in a number of different spinal or non-spinal procedures.

Figure 10:
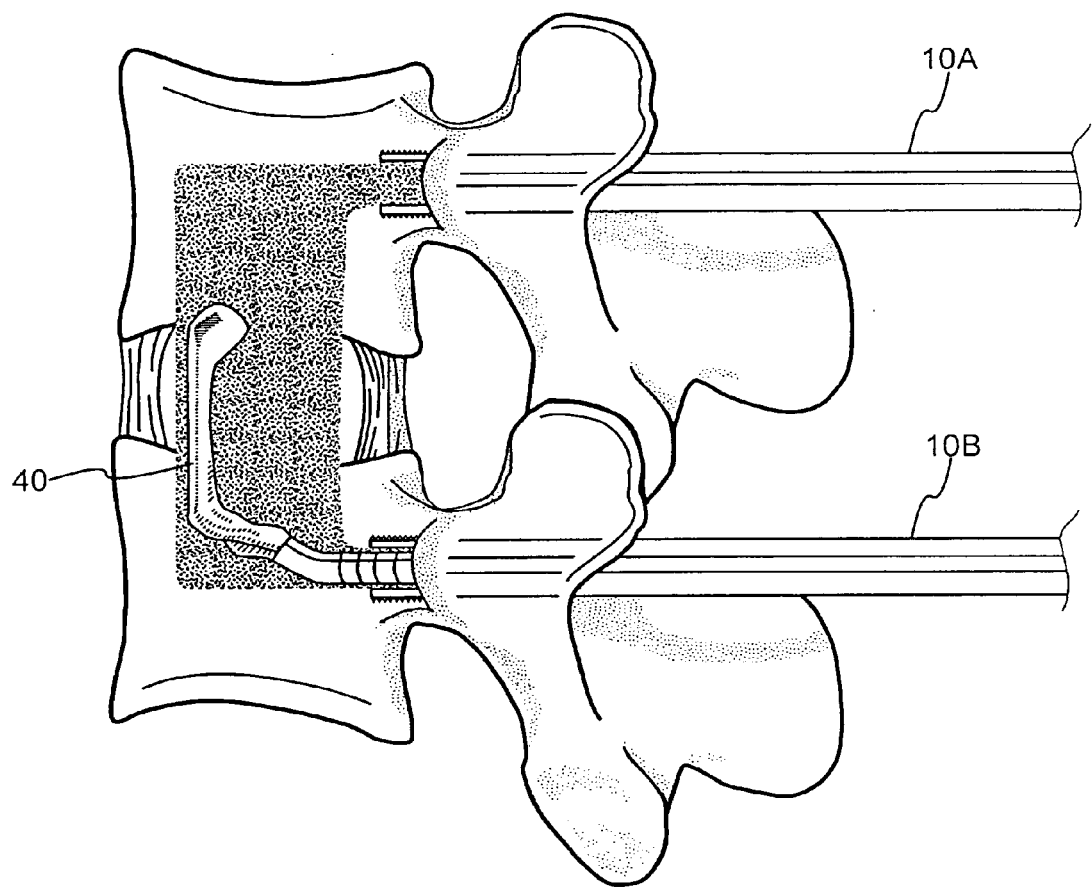
FIG. 10 is a view similar to FIG. 9 showing initial insertion of a balloon implant in the cavity.
Figure 11:
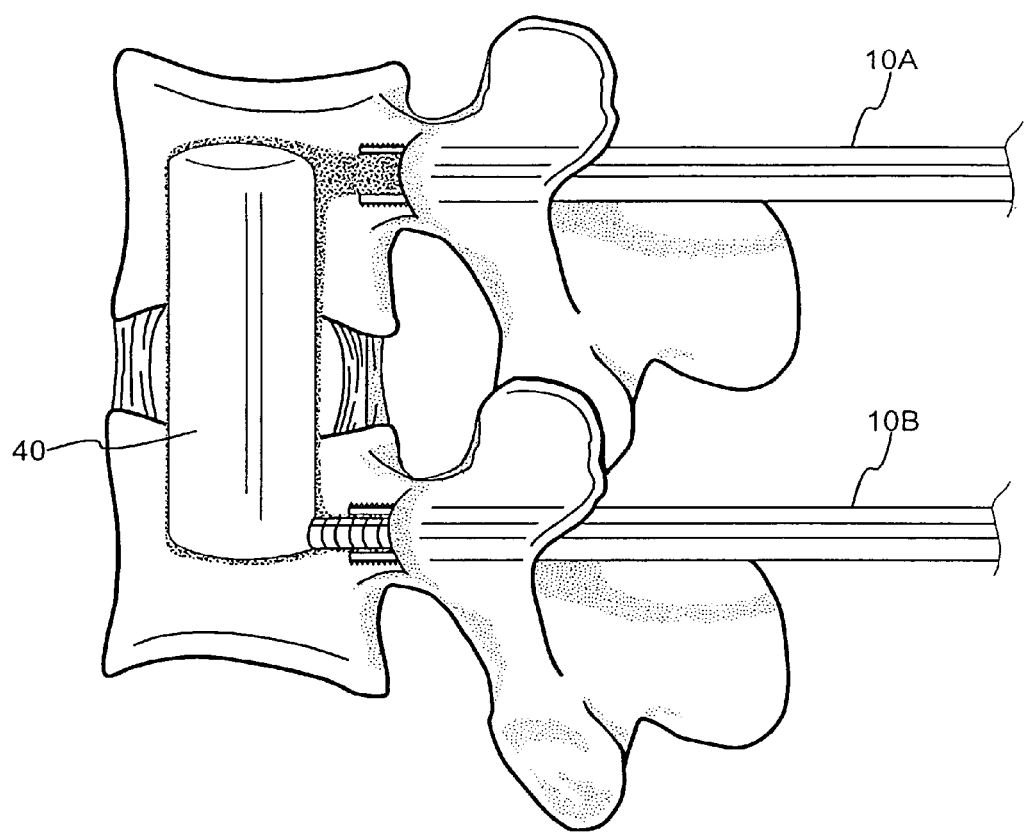
FIG. 11 is a view similar to FIG. 10 showing the balloon implant in an inflated state.
Figure 12:
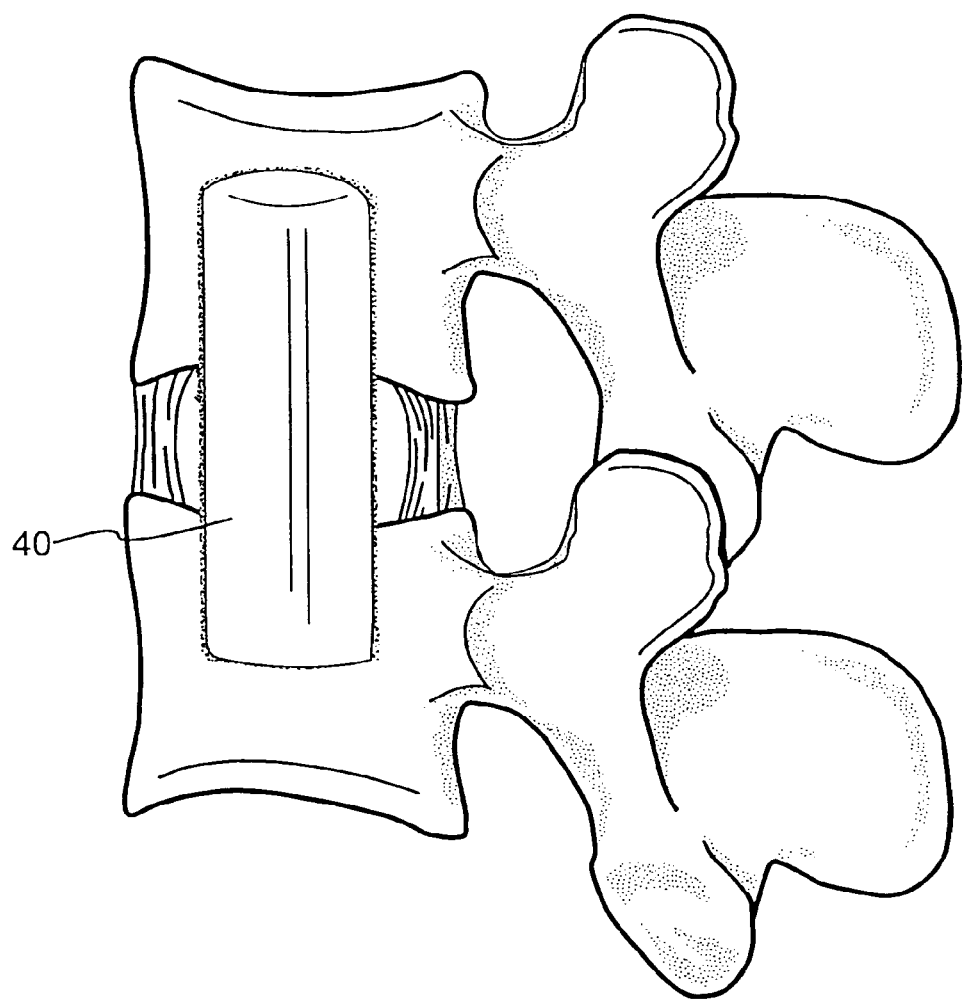
FIG. 12 is a view similar to FIG. 11 showing the balloon implant after removal of the guide tubes.

The system according to the invention also preferably includes at least one inflatable balloon implant 40 shown in FIGS. 10-12. The balloon implant 40 is configured to be filled with material to provide fusion in a cavity that is formed at least partially in an intervertebral disc, as described below. The balloon implant 40 is preferably made of a biodegradable substance such as collagen. The balloon implant 40 and the material used to fill it may include growth factors, such as bone morphogenic proteins or fibroplast growth factor, genetically modified cells for replacement therapy, or mesenchymal stem cells to further promote bony fusion.

The system according to the present invention could include other components, such as a device for providing suction and/or irrigation of a surgical site. Preferably, all or some of the components are made of permanent or disposable materials that are capable of being sterilized.

The present invention also includes one or more preferred methods of fusing a spinal region. These procedures are explained with reference to the structural embodiments described above. However, it should be understood that the method of the invention could be practiced with structure other than that disclosed herein. In addition, the structure of the present invention could be used with processes other than those described herein.

In one method according to the present invention, a patient is placed on an appropriate operating surface. Optionally, imaging equipment, such as fluoroscopy, is used to visualize a region of the spine. Small stab incisions are made in the back and a conventional drill is preferably used to drill a hole through corticle material on the outer surface of the pedicle of a vertebra.

Figure 4:
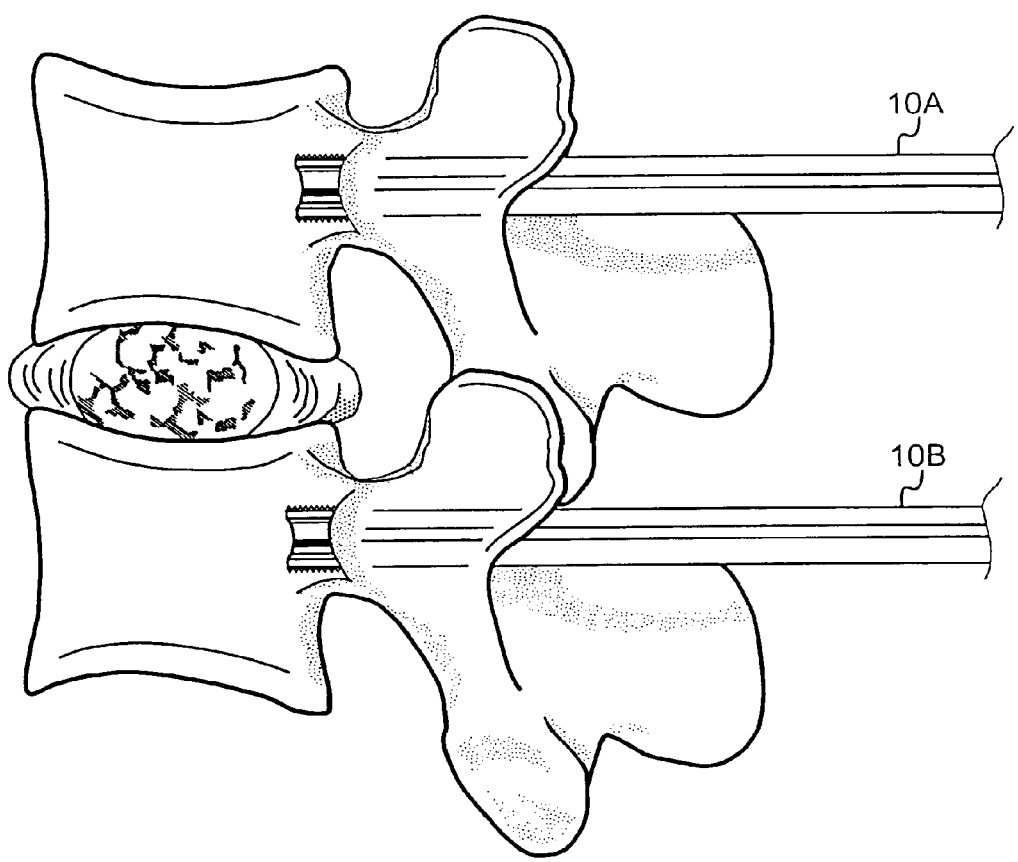
FIG. 4 is a view similar to that of FIG. 1 showing an initial step in one preferred procedure according to the present invention wherein guide tubes are inserted into the pedicles of adjacent vertebrae.

For the procedure shown in FIG. 4, a first hole is drilled in the pedicle of a first vertebra and a second hole is drilled in a pedicle of a second vertebra adjacent to the first vertebra. Although FIGS. 4-11 show these holes as being substantially parallel to the plane of the disc, the holes are preferably angled from about 30 degrees to about 45 degrees with respect to the plane of the disc so that the axes of the holes form an angle having a vertex at the disc.

A respective guide tube 10a, 10b is placed in contact with each of the vertebrae. Preferably, each guide tube 10a, 10b is releasably anchored in the corresponding pedicle hole by engaging the threads on the guide tube 10a, 10b in the vertebrae. Once the guide tubes 10a and 10b have been inserted, an X-ray, CT scan or other diagnostic scan could be used to localize the anatomical position of the tubes 10a and 10b, identify the best position for fusion and identify the best insertion points for subsequent instrumentation.

Figure 5:
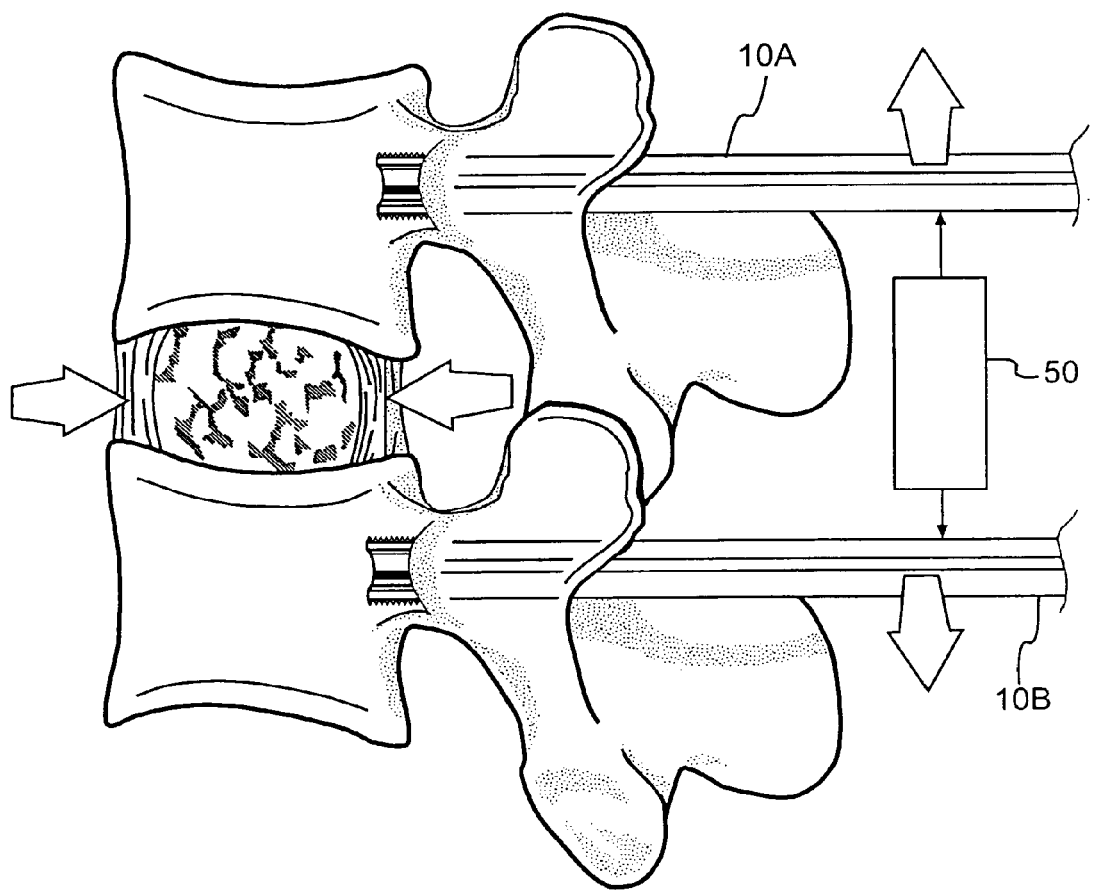
FIG. 5 is a view similar to that of FIG. 4 showing movement of the guide tubes to position the vertebrae.
Figure 6:
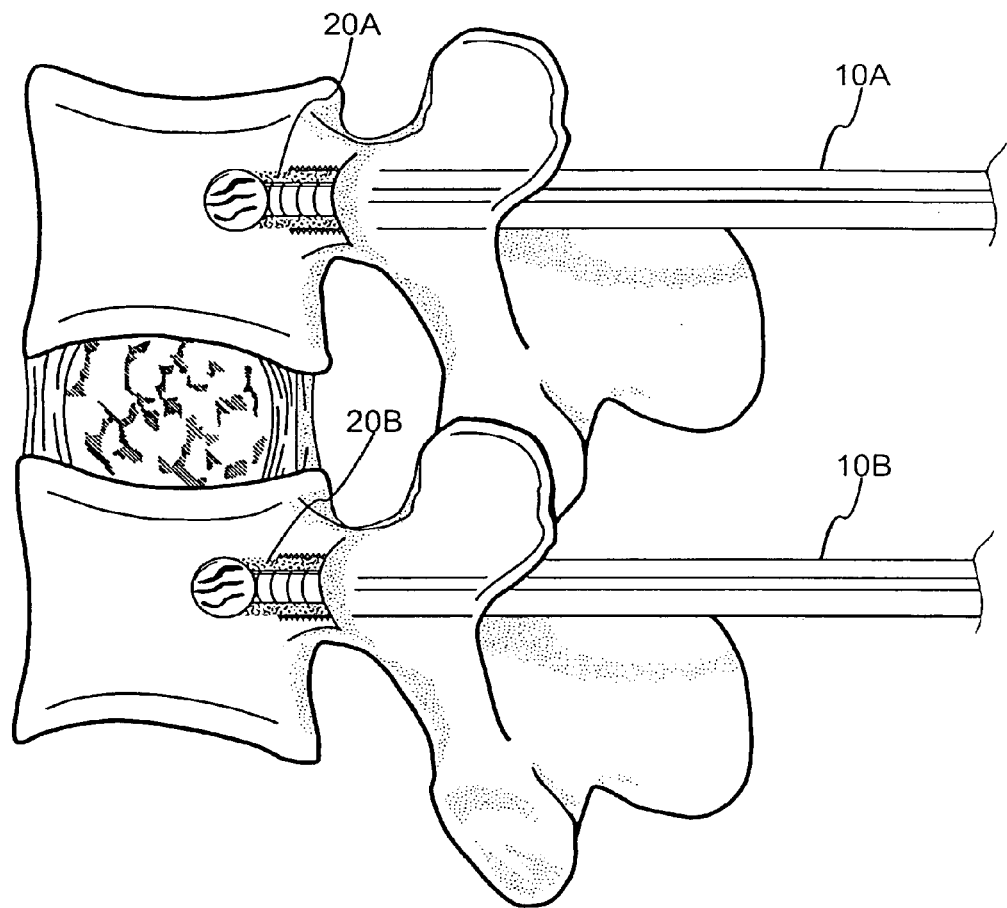
FIG. 6 is a view similar to that of FIG. 5 showing a pair of steerable drilling tools each passing through a respective one of the guide tubes.

After anchoring the guide tubes 10a and 10b, at least one of the guide tubes 10a and 10b is moved to thereby position one or more of the vertebrae. For example, as shown in FIG. 5, a distraction tool 50 is coupled to the guide tubes 10a and 10b to force the guide tubes 10a and 10b apart from one another and thereby distract one or more of the vertebrae away from the disc. The distraction tool 50 could be constructed in many different ways. For example, this device could have a ratchet adjustment.

In addition to moving the guide tubes 10a, 10b toward or away from each other, one or more of the anchored guide tubes 10a, 10b could be rotated (or translated) to thereby rotate (or translate) one or more of the vertebrae. Preferably, a computer-controlled surgical navigation device is used to determine the movement of the guide tubes, for example, by interacting with the tracking element 14 shown in FIG. 2. This preferably enables a surgeon to visualize the repositioning of the vertebrae.

Figure 7:
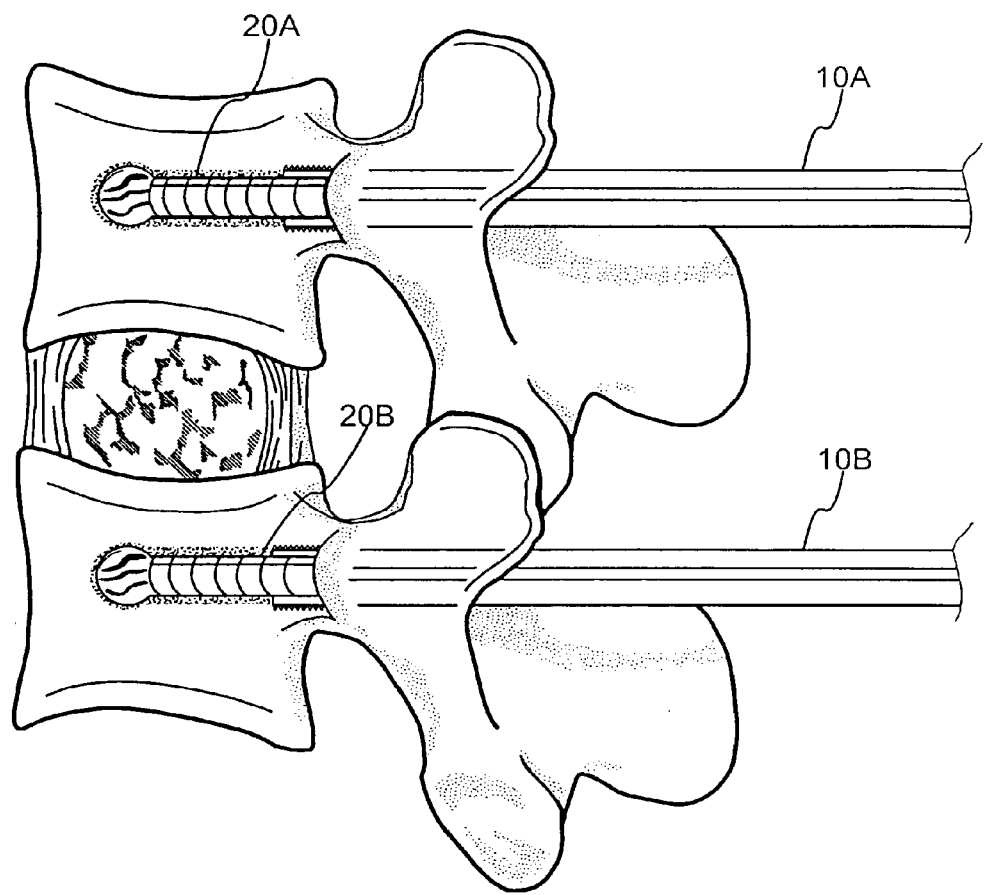
FIG. 7 is a view similar to FIG. 6 showing advancement of the steerable drilling tools to abrade vertebral material.
Figure 8:
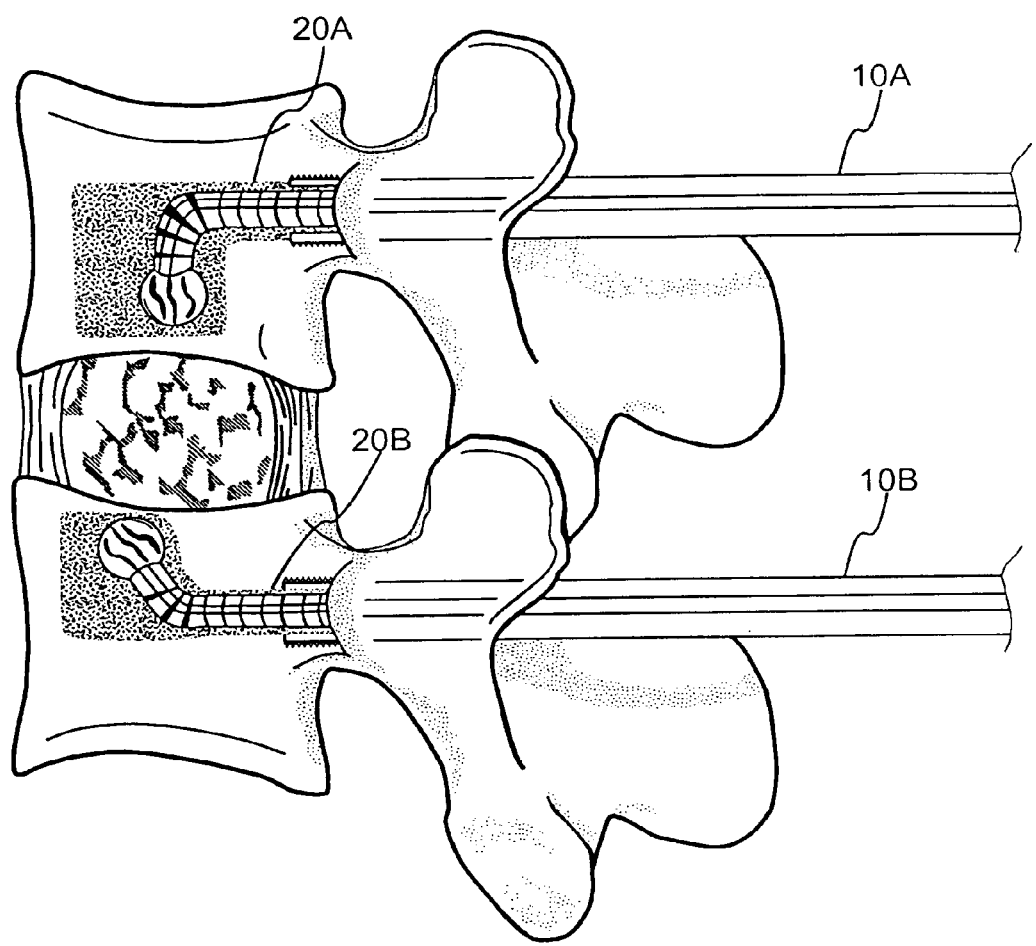
FIG. 8 is a view similar to FIG. 7 showing steering of the drilling tools and further abrasion of vertebral material.
Figure 9:
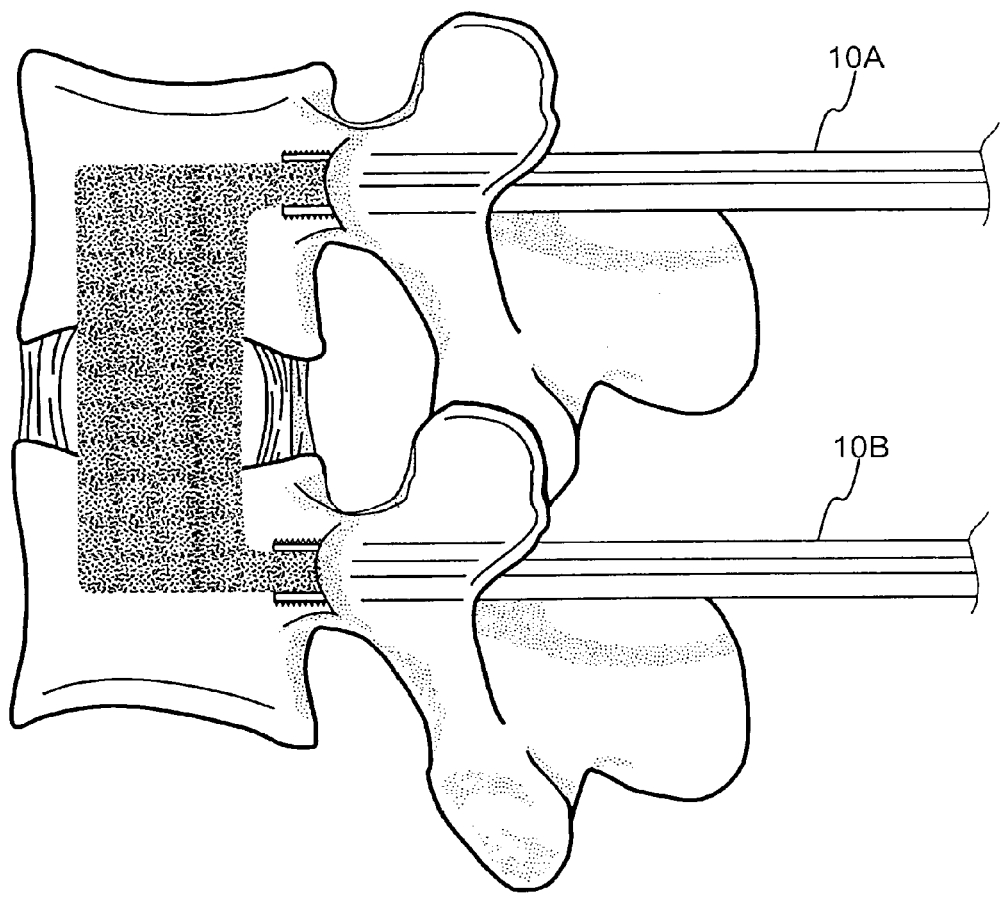
FIG. 9 is view similar to FIG. 8 showing a cavity created as a result of abrasion with the drilling tools.

One or more steerable drilling tools 20a and 20b are inserted though the guide tubes 10a and 10b. The drive member 24 (FIG. 3) of each drilling tool 20a, 20b is rotated to thereby rotate each bit 22. Each drilling tool is moved further through the guide tubes 10a and 10b, as shown in FIG. 7, and the bit 22 abrades material in the respective vertebra, including medullary material spaced away from the disc. As shown in FIG. 8, each of the drilling tools 20a and 20b are preferable steered toward the disc, for example by axially moving the steering element 32 (FIG. 3), and the drilling tools 20a and 20b abrade at least a portion of the end plates of the disc between the vertebrae.

The material abraded by the drilling tools 20a and 20b is preferably removed through one or both of the guide tubes 10a, 10b. For example, a suction and/or irrigation device could be passed into one of the tubes 10a and 10b, while one of the drill tools is passed through the other of the tubes 10a and 10b.

The position of the distal end of the drilling tools 20a and 20b is preferably determined, for example, by using a computer controlled surgical navigation device that interacts with the tracking element 34 (FIG. 3). After abrasion of all material, the drilling tools 20a and 20b are pulled out of the tubes 10a and 10b, and the further removal of any remaining loose material occurs via suction, irrigation, flexible forceps, or other means for clearing such loose material.

Eventually, all of the interior of the disc, including its nucleus, is removed to form a cavity extending through the disc and preferably into portions of the adjacent vertebrae. Preferably, none of the circumferential segments of the annulus fibrosis are abraded or removed during the procedure, such that at least a portion of the fibrosis extends around the cavity.

In a preferred practice of the invention, the inflatable balloon implant 40 is preferably inserted into the cavity via one of the guide tubes 10a and 10b. The balloon is preferably filled with a contrast agent, as shown in FIG. 11, and the balloon is viewed with appropriate imaging equipment, such as a fluoroscope. One possible imaging agent that could be used to inflate the balloon is OMNIPAQUE. Since the inflated balloon preferably fills the entire cavity, the imaging of the balloon can be used to evaluate whether the cavity is properly configured. It can also be used to ascertain proper anatomic alignment or position and to verify complete filling of the cavity. In the event that further material needs to be removed to enlarge the cavity, the implant 40 could be removed from the cavity, and abrasion with one or more of the steerable drilling tools could be continued.

When the cavity is properly formed, a flowable fusion substance is preferably passed into the cavity via one of the guide tubes 10a, 10b. Preferably, the fusion substance is a substance capable of solidifying such that it is no longer readily flowable. For example, the fusion substance could be a solidifying agent including polymethacrylate, such as methylmethacrylate or cranioplastic methacrylate, hydroxyapatite, another polymer, and/or a biological matrix. The flowable substance may include growth factors, such as bone morphogenic proteins or fibroplast growth factor, genetically modified cells for replacement therapy or mesenchymal stem cells to further promote bony fusion. In addition, the fusion substance could include antibiotics such as tobramycin, for example.

In one possible practice of the invention, the balloon implant used for the imaging is removed from the cavity before the fusion substance alone is passed into the cavity. Alternatively, the balloon implant 40 used for the imaging could be drained of the imaging agent and then filled with the fusion substance via one of the guide tubes 10a, 10b. In another alternate practice of the invention, the balloon implant 40 used for the contrast agent is removed from the cavity and another balloon implant is inserted in the cavity and filled with the fusion substance. Filling a balloon implant with the fusion substance is preferred in order to contain the fusion substance and prevent migration into unintended areas, such as the area near the spinal chord. After passing the fusion substance into the cavity, the tubes 10a and 10b are removed from the vertebrae.

Figure 13:
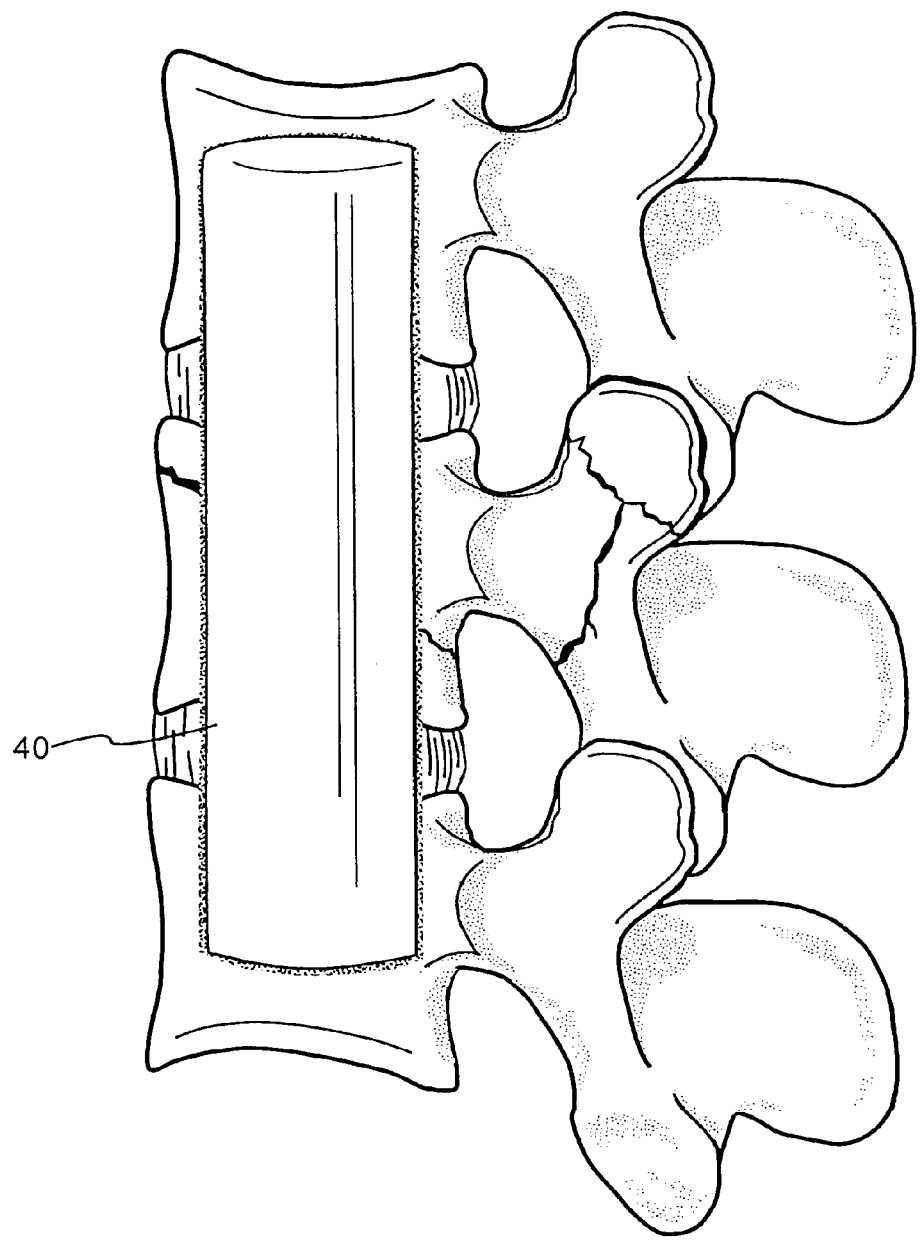
FIG. 13 is a view of an alternate embodiment of a balloon implant that is configured to extend along a cavity passing through a pair of adjacent discs.

FIG. 12 shows the balloon implant 12 in place after being filled with the flowable agent and after solidification of the fusion substance. FIG. 13 shows an alternate embodiment of a balloon implant 40a that is configured to fill a relatively larger cavity extending into two adjacent discs positioned near a spinal fracture.

In the preferred practice of the invention, the guide tubes 10a, 10b could be moved at various times during the procedure to reposition one or more of the vertebrae. For example, the movement shown in FIG. 5 could take place after the cavity is fully formed. In addition, the vertebrae could be retained in their repositioned state until the fusion substance solidifies.

Figure 14:
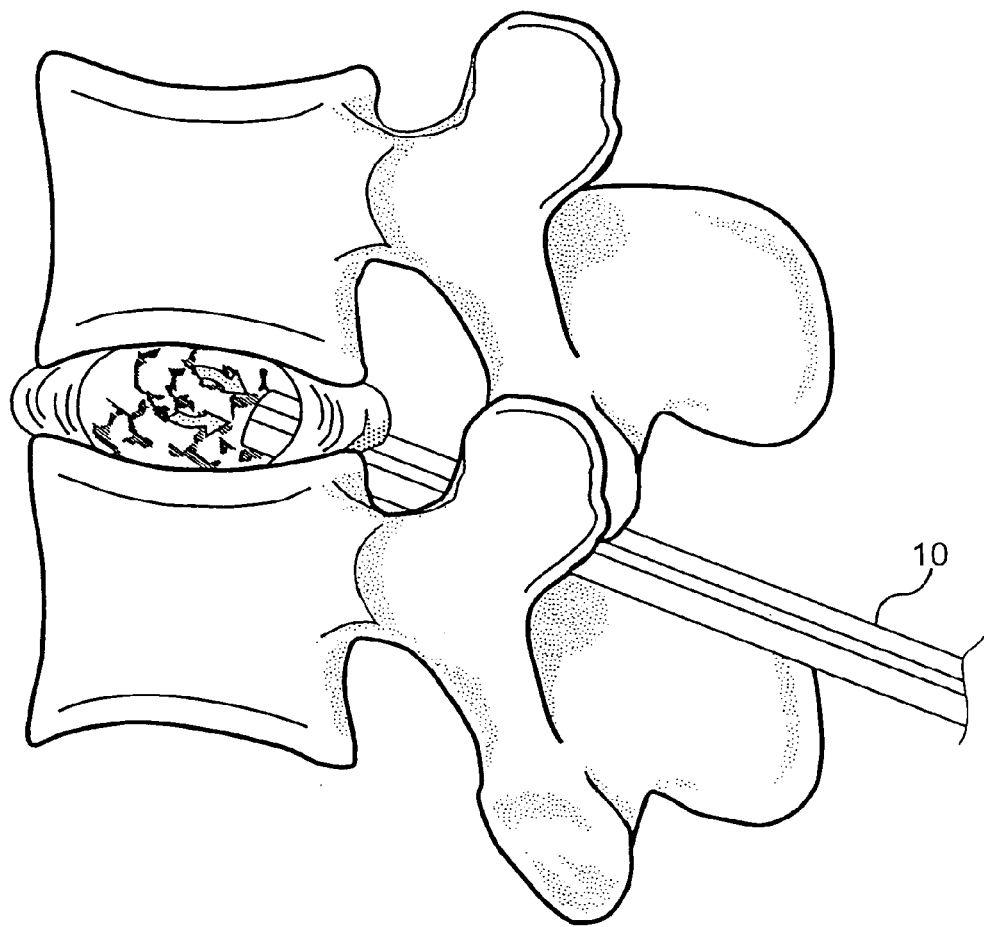
FIG. 14 is a view of an alternative procedure according to the present invention wherein a single guide tube is used to remove intervertebral disc material.
Figure 15:
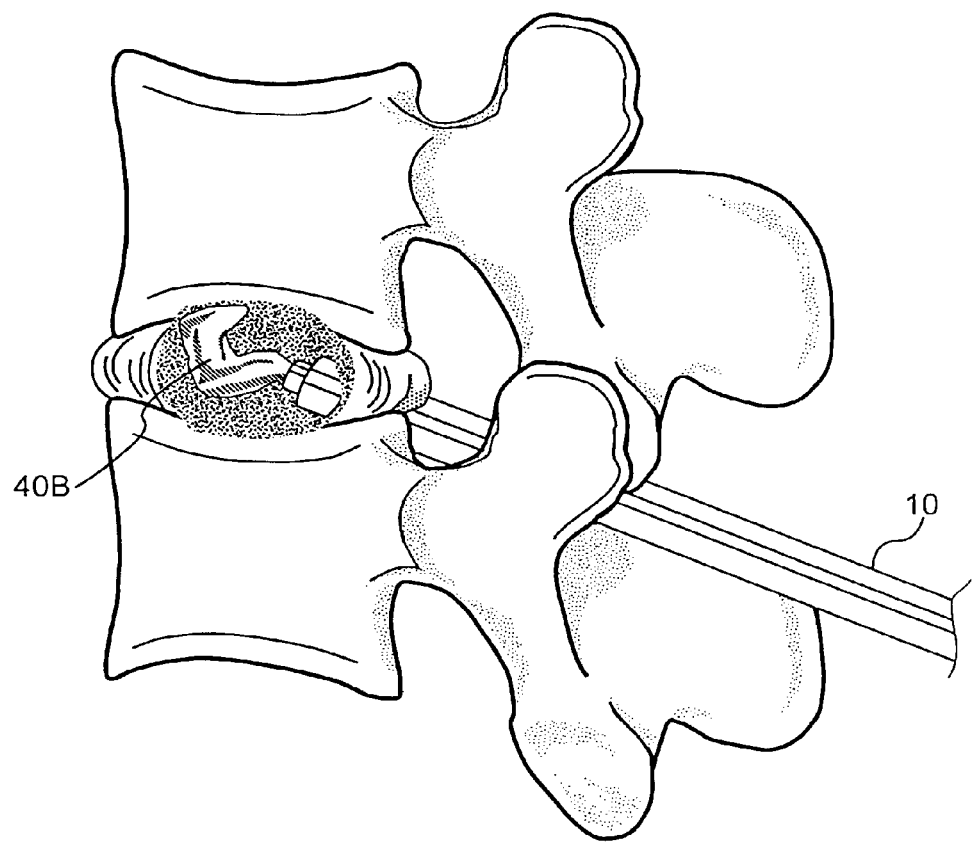
FIG. 15 is a view similar to FIG. 14 showing insertion of a balloon implant in a cavity formed at least partially in the disc.
Figure 16:
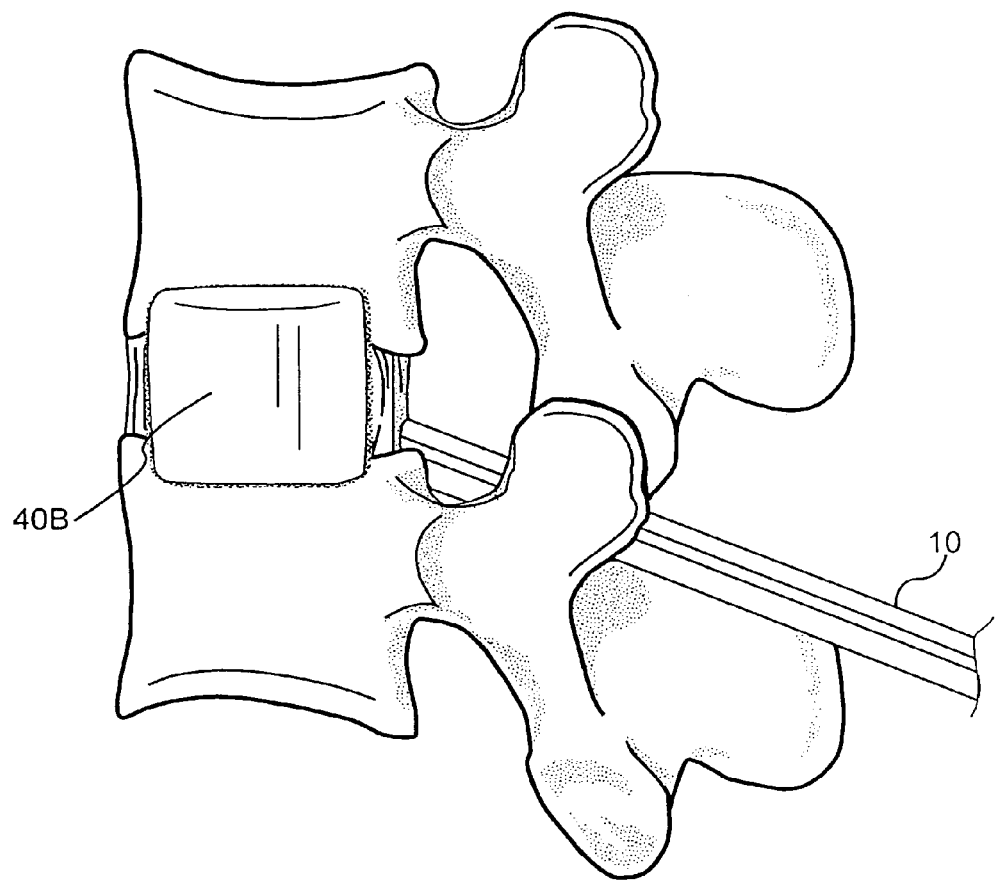
FIG. 16 is a view similar to FIG. 15 showing the balloon implant in an inflated state filling the cavity.
Figure 17:
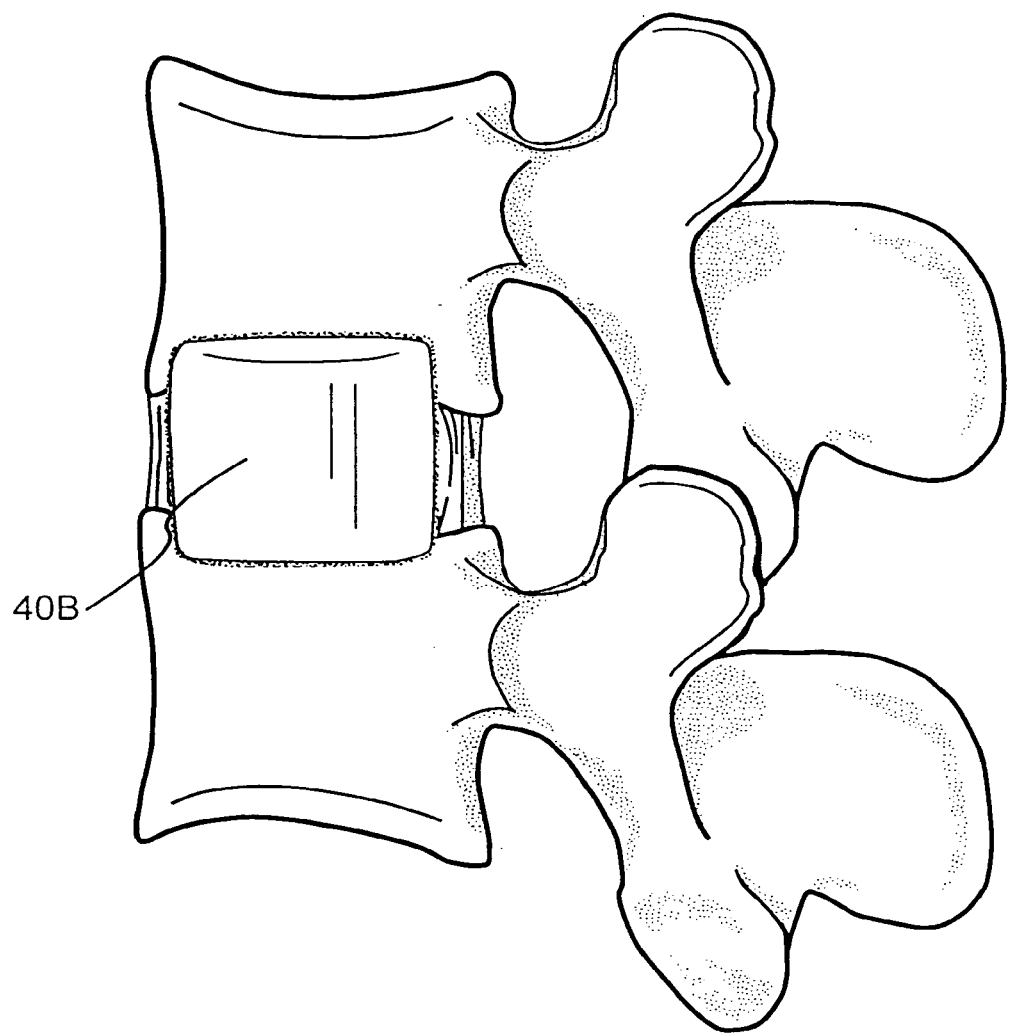
FIG. 17 is a view similar to FIG. 16 showing the balloon implant in place after removing the guide tube.

FIGS. 14-17 show an alternative procedure like that shown in FIGS. 4-13, but involving a single guide tube 10. As shown in FIG. 14, the guide tube 10 is used to remove the inner material from a disc with suction applied though the guide tube 10. As shown in FIGS. 15-17, a balloon is inserted into a cavity formed in the disc and eventually filled with the fusion substance to fuse the spinal region.

The method and apparatus according to the invention could be used for noninvasive or minimally invasive spinal disc distraction, rotation or translation and subsequent stabilization. The invention could be used for treatment of spinal disorders including, but not limited to, scoliosis, lordosis, kyphosis, spinal fractures, spinal instability, tumors, spinal degeneration due to disease, disc bulges, herniations, and tears. Preferably, the invention will stabilize the spine and correct anatomic misalignment caused by the above disorders. For example, the movement of one or more of the guide tubes to reposition one or more vertebrae could be used to correct scoliosis prior to spinal fusion.

The method and apparatus according to the present invention could be used for procedures in many different areas of the spine. Although the invention has particular advantages in association with procedures for the lower spinal area, the invention could also be used for procedures for the thoracic area or the cervical area, for example.

Preferably, the present invention shortens the time a patient is being operated on by speeding up the repair of the spinal disorders and thereby reduces risks associated with pre- and post-operative complications. The invention also preferably decreases pain by decreasing pressure on nerve roots, improves mobility, and improves long-term alignment of the spine, thereby providing improved outcomes for spinal disorder patients.

The invention could be used to fuse regions of various sizes. For example, the invention could be practiced to fuse two adjacent spinal discs or may be used across more than two.

There are a variety of different ways in which the various instruments could be guided during a procedure. For example, stereotactic guidance could be used.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A method of fusing a spinal region, the method comprising:
releasably anchoring a first guide tube in a first vertebra;
releasably anchoring a second guide tube in a second vertebra that is adjacent to said first vertebra;
moving at least one of said guide tubes to position the first and second vertebrae with respect to one another;
inserting a steerable drilling tool through one of said guide tubes;
steering the steerable drilling tool toward the disc between said two adjacent vertebrae;
abrading at least a portion of said disc with the drilling tool;
removing at least the abraded portion of said disc and a nucleus of said disc to form a cavity extending in at least said disc; and
placing an implant in said cavity, the implant being configured to provide fusion in said cavity.

2. The method of claim 1, wherein the implant is inflatable and wherein the placing of the implant includes inserting the balloon in said cavity in an uninflated state and inflating the balloon in the cavity.

3. The method of claim 1, wherein the abrading includes abrading vertebral material in the medullary area of the at least one of said adjacent vertebrae such that said cavity extends into said at least one of said adjacent vertebrae.

4. The method of claim 1 wherein said first and second guide tubes are both moved to position both of said first and second vertebrae.

5. A steerable drilling tool comprising:
a flexible tubular member having a proximal end portion, a plurality of hinge members, each of said hinge members coupling adjacent pairs of segments to permit relative pivotal movement of the segments in each said the pairs of segments, and a distal end portion;
a flexible, rotatable drive member in said tubular member;
a bit on the end of the rotatable drive member, the bit being rotated during rotation of the drive member and being located at the distal end portion of the tubular member; and
a steering element configured such that movement of the steering element varies the position of the distal end portion of said tubular member with respect to the remainder of the tubular member.

6. A method of fusing a spinal region, the method comprising:
removing at least a nucleus of an intervertebral disc to form a cavity extending in at least the disc;
inserting a balloon into the cavity;
inflating the balloon with a contrast agent;

viewing the balloon with imaging equipment to evaluate the cavity;

removing the contrast agent and the balloon from the cavity; and flowing a flowable fusion substance into the cavity, the fusion substance being configured to solidify to provide fusion in the cavity.

\* \* \* \* \*